US010980567B2

(12) United States Patent
Sahhar

(10) Patent No.: US 10,980,567 B2
(45) Date of Patent: *Apr. 20, 2021

(54) LUMBAR PUNCTURE ASSIST TOOL

(71) Applicant: Edward Via College of Osteopathic Medicine, Blacksburg, VA (US)

(72) Inventor: Hanna Samaan Sahhar, Spartanburg, SC (US)

(73) Assignee: Edward Via College of Osteopathic Medicine, Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/283,263

(22) Filed: Feb. 22, 2019

(65) Prior Publication Data

US 2019/0183523 A1 Jun. 20, 2019

Related U.S. Application Data

(63) Continuation of application No. 15/148,642, filed on May 6, 2016, now Pat. No. 10,245,068.

(60) Provisional application No. 62/158,040, filed on May 7, 2015.

(51) Int. Cl.
*A61B 17/34* (2006.01)

(52) U.S. Cl.
CPC ...... *A61B 17/3403* (2013.01); *A61B 17/3401* (2013.01); *A61B 2017/3407* (2013.01)

(58) Field of Classification Search
CPC ............ A61B 17/3401; A61B 17/3403; A61B 2017/3407; A61M 25/06
See application file for complete search history.

(56) References Cited

U.S. PATENT DOCUMENTS 5,308,352 A 5/1994 Koutrouvelis
8,204,575 B2 * 6/2012 Stetz ..................... A61B 90/39
600/424

* cited by examiner

*Primary Examiner* — Jason E Flick
(74) *Attorney, Agent, or Firm* — Keith A. Vogt; Keith Vogt, Ltd.

(57) ABSTRACT

The present invention provides a tool and method for performing a lumbar puncture. The tool may include a first arm and a second arm and may form a T-shape. The first arm may be longer than the second arm. Also included is a projection extending from one of the arms. The projection has a downward angle and a passageway that is sized to accommodate a needle. The tool is configured to maintain the perpendicular placement of a needle between vertebrae and a preferred angle of insertion of about 15° during a procedure.

15 Claims, 4 Drawing Sheets

LUMBAR PUNCTURE ASSIST TOOL

RELATED APPLICATIONS

This application claims the benefit of U.S. Provisional Application No. 62/158,040 filed May 7, 2015 and herein incorporated by reference.

STATEMENT REGARDING FEDERALLY SPONSORED RESEARCH & DEVELOPMENT

Not applicable.

INCORPORATION BY REFERENCE OF MATERIAL SUBMITTED ON A COMPACT DISC

Not applicable.

BACKGROUND OF THE INVENTION

A lumbar puncture (LP), also known as a spinal tap, is a diagnostic and/or therapeutic procedure performed by a doctor. The procedure is performed by inserting a hollow needle into the subarachnoid space in the lumbar area (lower back) of the spinal column. The subarachnoid space is the canal in the spinal column that carries cerebrospinal fluid (CSF) between the brain and the spinal cord.

A lumbar puncture may be performed for various reasons. The most common reason is to remove a small amount of CSF for examination and diagnosis of various disorders. CSF is tested for red and white blood cells, protein, glucose (sugar), clarity, color, and the presence of bacteria, viruses, or abnormal cells. Excess CSF may also be removed in patients who have an overproduction or decreased absorption of the fluid.

In addition, a lumbar puncture may be used to measure the pressure of the CSF, which flows freely between the spinal column and the brain. The doctor measures the pressure during a lumbar puncture using a special tube (called a manometer) that is attached to the lumbar puncture needle.

A lumbar puncture may also be performed therapeutically to inject medications directly into the spinal cord. Some medications that may be given via lumbar puncture (intrathecally) include: spinal anesthetics before a surgical procedure, contrast dye for X-ray studies (for example, myelography), or chemotherapeutic agents to treat cancer.

Currently, using the traditional "Surface Landmarks Technique" the degree of success in LP tap procedures depends on the level of training, experience and skills of the healthcare professional.

BRIEF SUMMARY OF THE INVENTION

In one embodiment, the present invention provides a device and method that creates a puncture directly into the spinal chord region, with proper placement, including both the perpendicular placement between vertebrae and appropriate angle of the needle, which are critical to success of the procedure and to prevent inadvertent damage to the tissues.

In other embodiments, the present invention provides a device and method to increase the probability of a successful atraumatic tap.

In other embodiments, the present invention provides a device and method that stabilize a needle during insertion and fluid collection. The present invention may be used as an adjunct to other techniques such as Fluoroscopy-guided LP and Ultrasound-guided LP.

In other embodiments, the present invention provides a device and method designed to assist healthcare professionals and medical students in performing lumbar puncture successfully and safely. Most failed taps are attributed to fault in the angle of the spinal needle with the back of the patient resulting in missing the spinal canal (Subarachnoid space) and ultimately a dry or bloody tap (if it punctures a blood vessel). The embodiments of the present invention provide a solution to this common fault by providing a guide that maintains a needle at the proper insertion angle throughout the procedure.

In other embodiments, the present invention provides a device and method that prevents variability between procedures and promotes needle stability, control of insertion, and control over the approximate depth of insertion.

In other embodiments, the present invention provides a device and method that keeps the operating field sterile and the needle steady while collecting spinal fluids or instilling medication such as chemotherapy drugs especially if the patient keeps moving the back (agitated and restless).

In other embodiments, the present invention provides a device and method that decrease complications as well as the discomfort and pain of a lumbar puncture.

In other embodiments, the present invention provides a device and method that decrease the need for Ultrasound-guided LP and thereby decrease cost and eliminate extra training.

In other embodiments, the present invention provides a device and method that decrease the need for Fluoroscopy-guided LP, decrease radiation exposure, and may be used as a training tool for medical students and other healthcare professionals.

In other embodiments, the present invention provides a device and method particularly useful in performing LP when surface landmarks may not be easily identified such as in obese, muscular, and agitated/restless patients.

In other embodiments, the present invention provides a device and method particularly useful in performing LP on difficult to palpate spinal (surface) anatomical landmarks and for pediatric patients.

In other embodiments, the present invention provides a device and method particularly useful in performing lumbar puncture at the spinal interspaces located between L3-L4 and L4-L5 vertebrae In other embodiments, the present invention provides radio-opaque markers imprinted in the tool that may be used with single x ray test as projections to locate landmarks, such as in special situations such as severe malformation of spine (scoliosis) without exposing a patient to excessive radiation as in fluoroscopy or moving the patient to an interventional radiology department. This embodiment is particularly useful with unstable patients.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

DETAILED DESCRIPTION OF THE INVENTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

Figure 1:
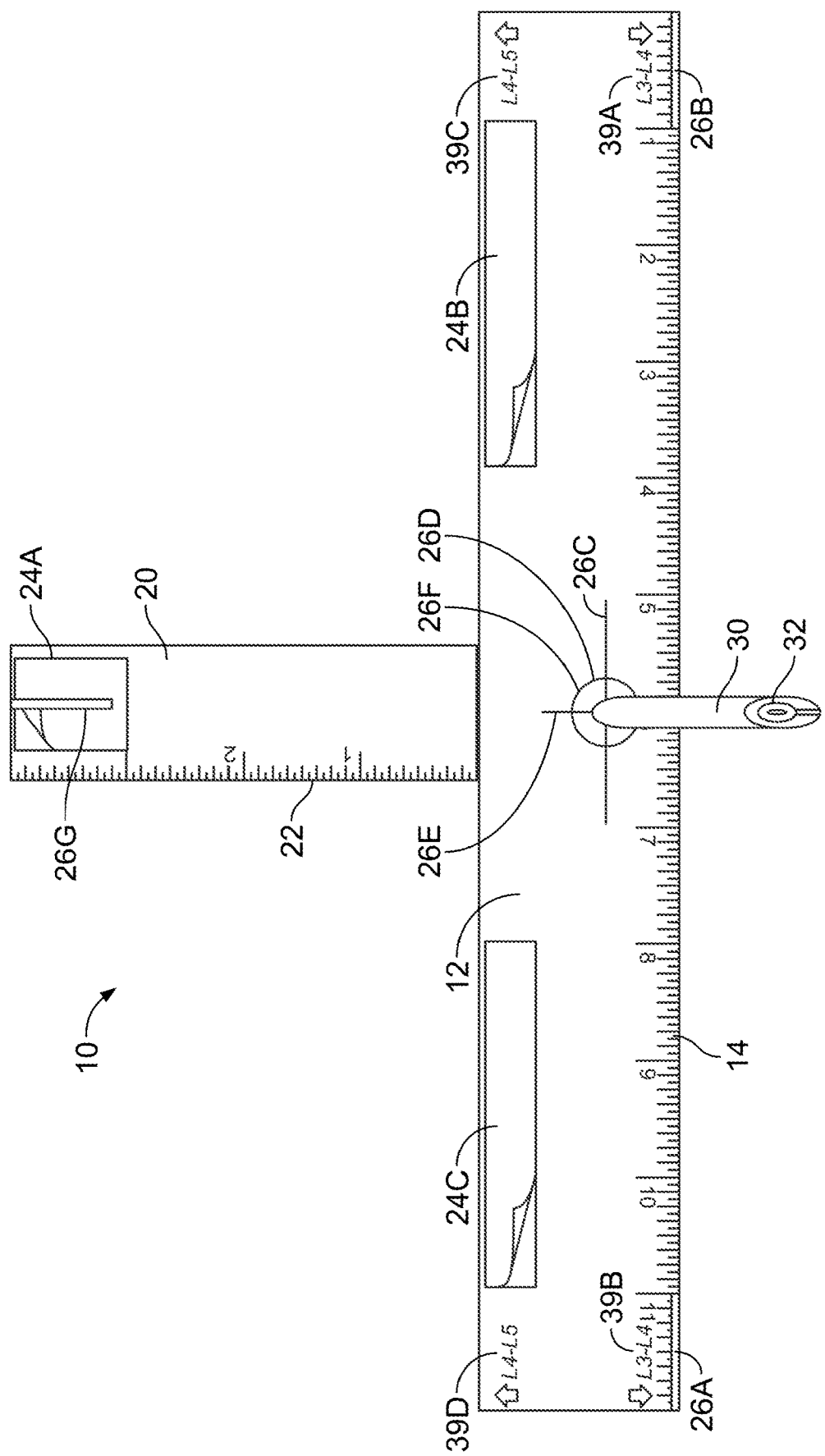
FIG. 1 illustrates a posterior view of an embodiment of the present invention.

As shown in FIG. 1, in one embodiment, the present invention provides a lumbar puncture tool 10 that has a long arm 12 which may be made of a transparent pliable plastic, latex-free, material. Markings that may be included on arm 12 include measurements in inches 14 although other scales such as centimeters may be used as well. Lumbar puncture device 10 may also include a short arm 20 which may be made of a transparent pliable plastic, latex-free, material. Arms 12 and 20, in a preferred embodiment, form a T-shape with arm 12 being the long arm and arm 20 being the short arm. Arms 12 and 20 may have adhesive sections 24A-24C to assist in securing device 10 in position on a patient.

Markings that may be included on arm 20 include measurements in inches 22 although other scales such as centimeters may be used as well. Other markings that may be used on arms 12 and 20 include radio-opaque markers 26A-26G which may be used to assist in positioning the device. Radio-opaque markers 26A-26G imprinted in the tool may be used with one or more x-ray tests as projections to locate landmarks, such as in special situations such as severe malformation of spine (scoliosis) without exposing a patient to excessive radiation as in fluoroscopy or moving the patient to an interventional radiology department. This embodiment is particularly useful with unstable patients. As shown, to assist in positioning the tool, radio-opaque markers 26A-26G may consist of straight, vertical, horizontal and intersecting lines as well as circles, squares and other geometric shapes.

Figure 2:
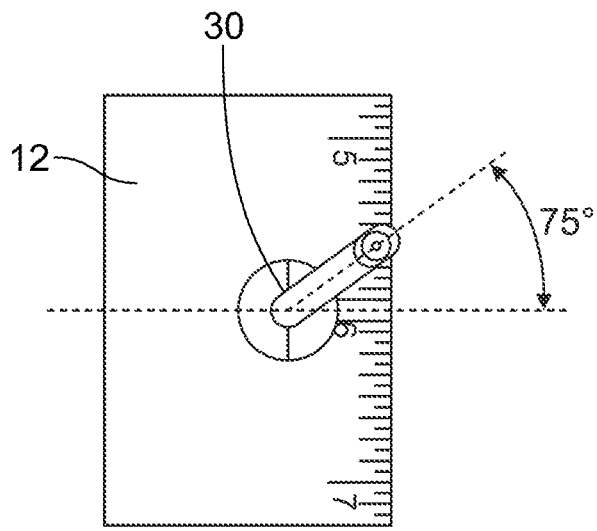
FIG. 2 is an exploded view showing a projection that may be used with an embodiment of the present invention.
Figure 3:
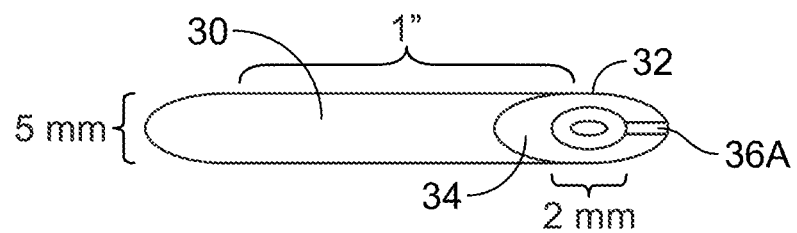
FIG. 3 is an exploded view showing a projection that may be used with an embodiment of the present invention.
Figure 4:
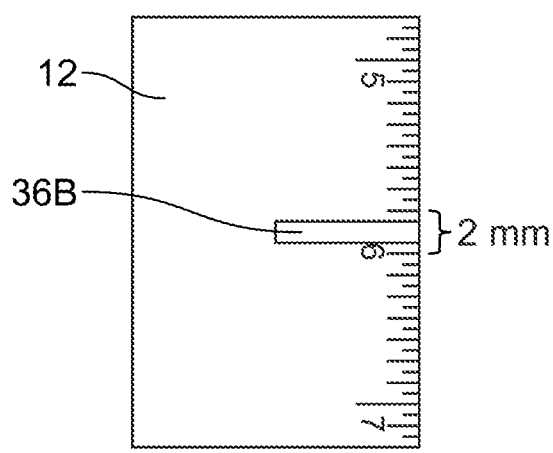
FIG. 4 is an exploded view showing use of a keyhole that may be used with an embodiment of the present invention.

As shown in FIGS. 1-3, lumbar puncture device 10 includes a conduit, post or projection 30. Projection 30 includes passageway 32 that extends through projection 30. Projection 30 may be resilient and made of hard rubber to resist bending. As shown in FIGS. 2-3, a preferred angle for projection 30 is 75° and a preferred length is one inch. In another preferred embodiment, the angle for projection 30 is between 65° and 85°. In other embodiments, projection 30 is angled to promote the insertion of a needle in the spinal interspace between vertebrae and is generally angled in a downward direction so that the proximal end of the needle will be directed toward the head of the patient. In other embodiments, projection 30 is bendable. In other embodiments, projection 30 is not bendable and is used to guide a needle during a lumbar puncture. Maintaining proper placement, including both the perpendicular placement between vertebrae and appropriate angle of the needle, is critical to success of the procedure and to prevent inadvertent damage to the tissues.

Projection 30 may be integral with either arm but is preferably located on the lower portion of arm 12 in a central location. Projection 30 may be attachable to arm 12 and face 34 may be angled at the desired angle to properly position projection 30 on arm 12. In a preferred embodiment of the present invention, face 34 has a downward angle of 15° or about 15° as defined from a vertical axis located between the upper edge and lower edge of arm 12.

Attachment of projection 30 to arm 12 may be accomplished by forming a key 36A on projection 30 and keyhole 36B in arm 12. This arrangement may be reversed as well and other known mechanisms of attachment may be used as well.

Figure 5:
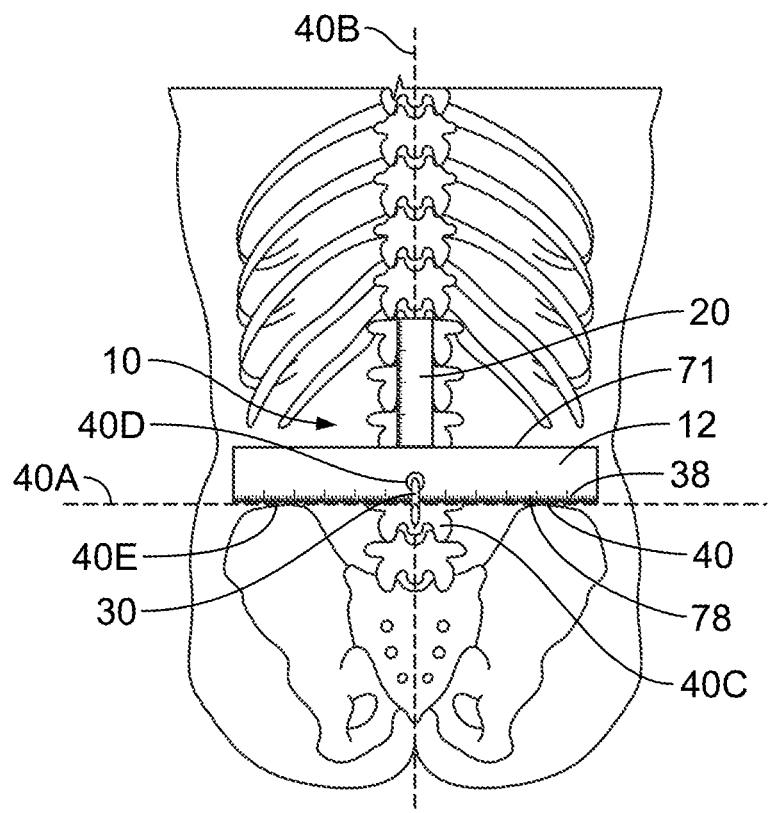
FIG. 5 illustrates how an embodiment of the present invention may be used to perform a lumbar puncture at the spinal interface between the L3 and L4 vertebrae.
Figure 6:
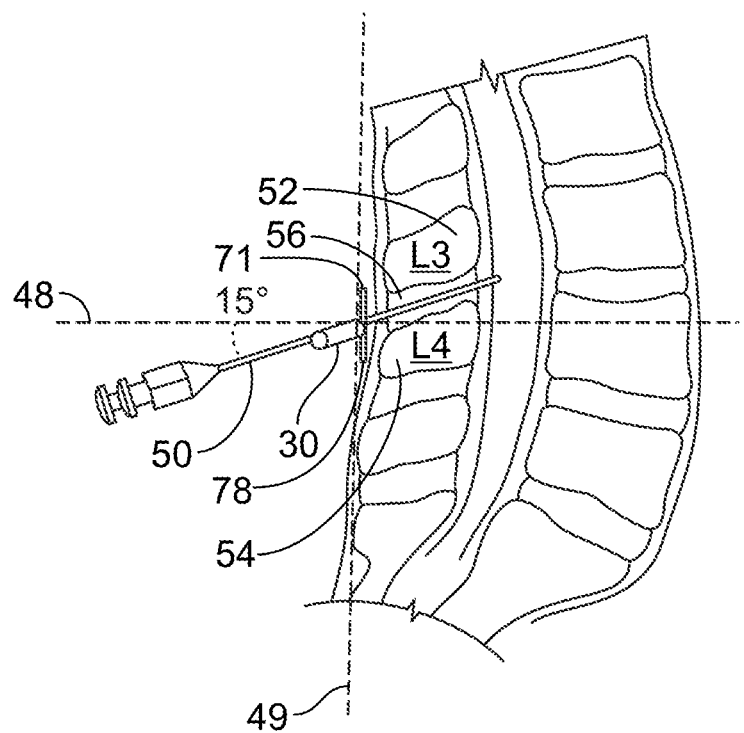
FIG. 6 illustrates a lateral view showing how an embodiment of the present invention may be used to perform a lumbar puncture at the spinal interface between the L3 and L4 vertebrae.

In use, as shown in FIGS. 5-6, lumbar puncture device 10 may use as an anatomical reference line 40A that crosses the right and left Superior Iliac Crests, line 40B which crosses the middle of the posterior spinous processes, location 40C which is the body of the 4th Lumbar vertebra (L4), location 40D which is the body of the L3-L4 spinal interspace, and locations 40E which are the Superior aspect of Iliac Crests (right & left). In a preferred embodiment for using lumbar puncture device 10, a first step is to locate the insertion point. A preferred point should be half way between L3 and L4 posterior spinous processes. The inner opening of projection 30 should cover this point. As shown in FIGS. 1 and 5, lower edge 38 of long arm 12 of tool 10 should be in line with line 40A that connects the superior aspect of the iliac crests. Short arm 20 of tool 10 should face upward in the center of the back on line 40B which crosses the posterior spinous processes. Markings 14, 22, and 26A-26G may be used to assist in precisely positioning tool 10.

Figure 7:
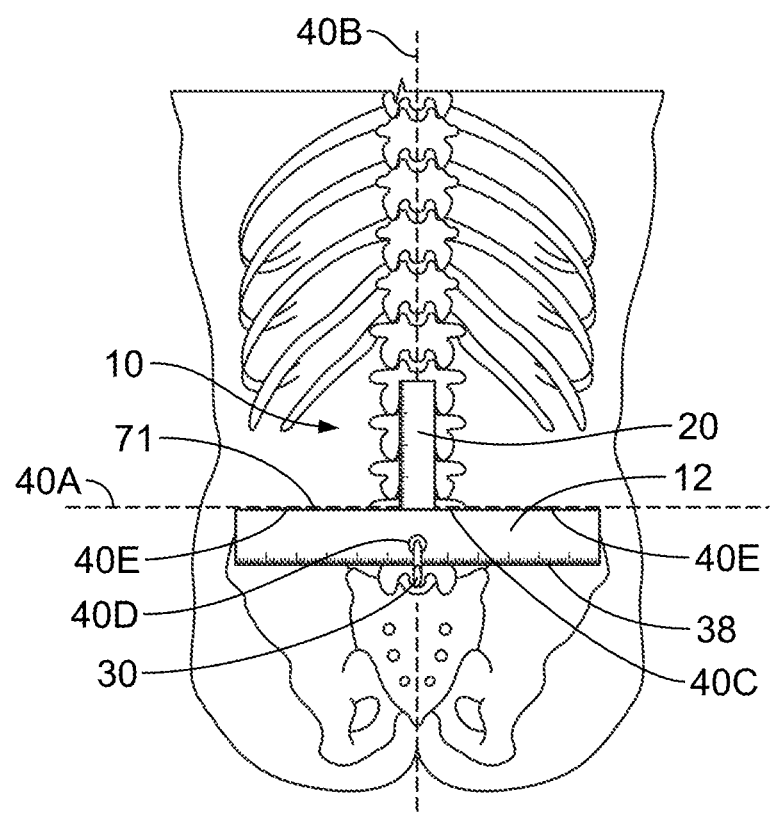
FIG. 7 illustrates how an embodiment of the present invention may be used to perform a lumbar puncture at the spinal interface between the L4 and L5 vertebrae.

As shown in FIG. 6, by prepositioning projection 30 at a downward angle of 15° from axis 48 or 75° from axis 49, needle 50 is able to pass through spinal interspace 56 between the L3 vertebra 52 and the L4 vertebra 54. As also shown in FIGS. 6 and 7, projection 30 may have a downward angle from upper edge 71 to lower edge 38 of arm 12 that may be 15° or about 15°.

Another advantage of the present invention, as shown in FIG. 5, is that projection 30 will maintain a needle in a position that is perpendicular to sagittal plane 40B. In other words, projection 30 prevents the needle from deviating off line 40B, such as towards one of the Iliac Crests (right or left).

A preferred needle insertion depth for adults is: depth (cm)=1+[17×(weight (Kg)/Height (cm))]*. A recommended needle size to use with tool 10 is a: 20 GA 4.5 IN 0.9×115 mm OR 22 GA 4.5 IN 0.7×115 mm (maximum gauge 14 GA) (minimum length 4.5 IN for >12 years of age).

A preferred method of use for inserting a needle into the spinal interspace between the L4 and L5 vertebra is to first find the insertion point. A preferred point should be half way between L4 and L5 posterior spinous processes. The inner opening of projection 30 should cover this point. Markings 14, 22, and 26A-26G may be used to assist in precisely positioning tool 10.

Next, as shown in FIG. 7, upper edge 71 of long arm 12 of tool 10 should be in line with line 40A that connects the superior aspect of the iliac crests. Short arm 20 of tool 10 should face upward in the center of the back on line 40B which crosses the posterior spinous processes. The process for the insertion of a needle is the same as described above.

The distance between edge 38 and edge 71 is such that it generally represents a distance that enables insertion of a needle into the two spinal interspaces described above. This enables a user to easily and quickly access both spaces during a lumbar puncture procedure if desired. Markings 39A-39D may be used as references for the particular edge to be used for a designated spinal interspace as shown in FIG. 1.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. A lumbar puncture device comprising:
   a first arm and a second arm forming a T-shape, said first arm having a surface defined by an upper edge, a lower edge, and opposing side edges;
   said first arm longer than said second arm;
   a projection having a first face and a second face, said faces separated by an elongated body;
   said first face adapted to engage said first arm and said projection extends from said first arm;
   a passageway having an entrance and exit, said passageway extends through said projection;
   said projection has a downward angle with respect to said first arm, said downward angle formed by locating said exit closer to said upper edge than said entrance; and
   said projection is attached to said first arm and extends downwardly from said first arm and said downward angle of said projection is in a vertical plane that is perpendicular to said lower edge.

2. The lumbar puncture device of claim 1 wherein said upper edge locates said device in a position where said passageway is in a position to guide a needle through a spinal interspace located between the L4 and L5 vertebrae and said lower edge used to locate said device in a position where said passageway is in a position to guide a needle through a spinal interspace located between the L3 and L4 vertebrae.

3. The lumbar puncture device of claim 2 wherein said projection has a downward angle of 75° as measured from said lower edge to said projection.

4. The lumbar puncture device of claim 3 wherein said projection is attached to said first arm at a 75° angle.

5. The lumbar puncture device of claim 1 wherein said projection is located on a lower portion of said first arm in a central location.

6. The lumbar puncture device of claim 5 wherein said projection is attached to said first arm at a predetermined angle.

7. The lumbar puncture device of claim 1 wherein said first face attached to said first arm has an angled planar surface, said surface of said first arm is a planar surface, said planar surfaces of said first face and said first arm are attached together.

8. The lumbar puncture device of claim 7 wherein said angled planar surface of said face positions said projection at an angle of about 75° as measured from said lower edge to said projection.

9. The lumbar puncture device of claim 8 wherein said projection has a downward angle of about 75° as measured from said lower edge to said projection.

10. The lumbar puncture device of claim 8 wherein said projection is located on the lower portion of said first arm.

11. The lumbar puncture device of claim 9 wherein said about 75° angle of said projection is in a vertical plane that is perpendicular to said lower edge.

12. The lumbar puncture device of claim 1 wherein said first face has a downward angle of about 15° from said upper edge to said lower edge of said first arm.

13. A method of accessing the spinal interspace between a L4 and L5 vertebra and a second spinal interspace between the L3 and L4 vertebra of a patient comprising the steps of:
   providing a planar lumbar puncture device having a T-shape formed by a longer arm and a shorter arm;
   locating said puncture device directly on the back of a patient;
   said longer arm having an upper edge and a lower edge, said upper edge used to locate said device into position by using iliac crests as landmarks to permit a needle to access the spinal interspace between the L4 and L5 vertebrae;
   said lower edge used to locate said device into position by using iliac crests as landmarks to permit a needle to access the spinal interspace between the L3 and L4 vertebrae;
   said longer arm includes a projection attached to said longer arm and having a passageway therein adapted to receive the needle and said projection positioned on said longer arm so as to guide the needle through the spinal interspace during insertion of the needle through the passageway; and
   said projection has a downward angle of 75° C. as measured from said lower edge to said projection and said about 75° C. angle of said projection is in a vertical plane that is perpendicular to said lower edge.

14. The lumbar puncture device of claim 13 wherein said projection has an angled planar face that is attached to a planar surface on said arm, said angled planar face positions said projection at an angle of about 75° as measured from said lower edge to said projection.

15. The lumbar puncture device of claim 14 wherein said projection has a downward angle of about 75° as measured from said lower edge to said projection.

* * * * *